United States Patent [19]
Tanaka et al.

[11] Patent Number: 6,111,127
[45] Date of Patent: Aug. 29, 2000

[54] PROCESS FOR THE PREPARATION OF UNSATURATED PHOSPHONIC ACID ESTER

[75] Inventors: Masato Tanaka, c/o National Institute of Materials and Chemical Research of 1, Higashi 1-chome, Tsukuba-shi, Ibaraki-ken; Li-Biao Han, Tsukuba, both of Japan

[73] Assignees: Agency of Industrial Science & Technology; Masato Tanaka, both of Japan

[21] Appl. No.: 09/394,626

[22] Filed: Sep. 13, 1999

[30]   Foreign Application Priority Data

Mar. 8, 1999 [JP] Japan ................................. 11-059933
Mar. 8, 1999 [JP] Japan ................................. 11-060093

[51] Int. Cl.$^7$ ........................................................ C07F 9/40
[52] U.S. Cl. .......................................... 558/137; 558/217
[58] Field of Search ............................................. 558/137

[56]   References Cited

U.S. PATENT DOCUMENTS 3,673,285   6/1972   Lin .......................................... 558/137
5,693,826  12/1997   Tanaka et al. .............................. 549/6

*Primary Examiner*—Michael G. Ambrose
*Attorney, Agent, or Firm*—Lorusso & Loud

[57]   ABSTRACT

A process for the preparation of an unsaturated phosphonic acid ester of the formula:

$$R^1CH=C(R^2)P(=O)(OR^3)_2$$

wherein an acetylene compound of the formula:

$$R^1C\equiv CR^2$$

is reacted with a secondary phosphite of the formula:

$$HP(=O)(OR^3)_2$$

in the presence of a palladium complex catalyst. The process is characterized in that the reaction is performed in the presence of water or in that the palladium complex catalyst contains, as a ligand, a 1,3-bisphosphinopropane of the formula:

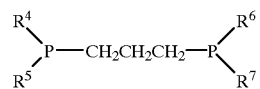

wherein $R^4$, $R^5$, $R^6$ and $R^7$ stand, independently from each other, for an alkyl group, a cycloalkyl group, an aralkyl group or an aryl group.

5 Claims, No Drawings

PROCESS FOR THE PREPARATION OF UNSATURATED PHOSPHONIC ACID ESTER

This invention relates to a process for the preparation of an unsaturated phosphonic acid ester.

Unsaturated phosphonic esters are useful in the fields of medicaments and agricultural chemicals as intermediate compounds for the production of physiologically active substances. One known method of producing a phosphonic ester is substitution of the corresponding unsaturated halogenated compound with a secondary phosphite in the presence of a base. The known method has a problem because a large amount of a salt of the base with HX (X represents a halogen atom) is formed. Additionally, the unsaturated halogenated compound is poisonous and is not easily commercially available.

U.S. Pat. No. 5,693,826 discloses a process for the production of an unsaturated phosphonic ester expressed by the following formula:

$$R^1CH = C(R^2)P( = O)(OR^3)_2$$

wherein R1 and R2 are independently selected from a hydrogen atom, an alkyl group, a cycloalkyl group, an aryl group, a heteroaryl group, an aralkyl group, an alkenyl group, an alkoxy group, an aryloxy group and a silyl group and R3 is selected from the group consisting of an alkyl group, a cycloalkyl group, an aralkyl group and an aryl group. The process includes reacting an acetylene compound expressed by the following formula:

$$R^1C \equiv CR^2$$

wherein $R^1$ and $R^2$ are as defined above, with a secondary phosphite of the following formula:

$$HP( = O)(OR^3)_2$$

wherein $R^3$ is as defined above, in the presence of a palladium complex catalyst.

The above process has been found to have a problem in actual production unsaturated phosphonic acid ester on an industrial scale because the reaction rate and/or selectivity are not fully satisfactory.

The present invention has been made in view of the problem of the conventional method.

In accordance with the present invention, there is provided a process for the preparation of an unsaturated phosphonic acid ester of the following formula (I):

$$R^1CH = C(R^2)P( = O)(OR^3)_2 \quad (I)$$

wherein $R^1$ and $R^2$ stand, independently from each other, for a monovalent group selected from hydrogen atom, an alkyl group, a cycloalkyl group, an aryl group, a heteroaryl group, aralkyl group, an alkenyl group, an alkoxy group, an aryloxy group and a silyl group and $R^3$ stands for an alkyl group, a cycloalkyl group, an aralkyl group or an aryl group, comprising reacting an acetylene compound of the following formula (II):

$$R^1C \equiv CR^2 \quad (II)$$

wherein $R^1$ and $R^2$ are as defined above, with a secondary phosphite of the following formula (III):

$$HP( = O)(OR^3)_2 \quad (III)$$

wherein $R^3$ is as defined above, in the presence of a palladium complex catalyst, characterized in that said reaction of the acetylene compound with the secondary phosphite is performed in the presence of water.

In another aspect, the present invention provides a process for the preparation of an unsaturated phosphonic acid ester of the following formula (I):

$$R^1CH = C(R^2)P( = O)(OR^3)_2 \quad (I)$$

wherein $R^1$ and $R^2$ stand, independently from each other, for a monovalent group selected from hydrogen atom, an alkyl group, a cycloalkyl group, an aryl group, a heteroaryl group, aralkyl group, an alkenyl group, an alkoxy group, an aryloxy group and a silyl group and $R^3$ stands for an alkyl group, a cycloalkyl group, an aralkyl group or an aryl group, comprising reacting an acetylene compound of the following formula (II):

$$R^1C \equiv CR^2 \quad (II)$$

wherein $R^1$ and $R^2$ are as defined above, with a secondary phosphite of the following formula (III):

$$HP( = O)(OR^3)_2 \quad (III)$$

wherein $R^3$ is as defined above, characterized in that said palladium complex catalyst contains, as a ligand, a 1,3-bisphosphinopropane of the following formula (IV):

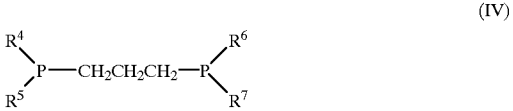

wherein $R^4$, $R^5$, $R^6$ and $R^7$ stand, independently from each other, for an alkyl group, a cycloalkyl group, an aralkyl group or an aryl group.

Preferred embodiments of the present invention will now be described below.

The secondary phosphite used in the process of the present invention is represented by the formula (III):

$$HP( = O)(OR^3)_2 \quad (III)$$

wherein $R^3$ stands for:

(a) an alkyl group preferably having 1–6 carbon atoms, more preferably 1–4 carbon atoms, such as methyl, ethyl, propyl or hexyl;

(b) a cycloalkyl group preferably having 3–12 carbon atoms, more preferably 5–6 carbon atoms, such as cyclohexyl, cyclooctyl or cyclododecyl;

(c) an aralkyl group preferably having 7–13 carbon atoms, more preferably 7–9 carbon atoms, such as benzyl, phenethyl, phenylbenzyl or naphthylmethyl; or (d) an aryl group preferably having 6–14 carbon atoms, more preferably 6–12 carbon atoms, such as phenyl, naphthyl, substituted phenyl (e.g. tolyl or benzylphenyl) or substituted naphthyl (e.g. methylnaphthyl).

The acetylene compound used in the process of the present invention is represented by the formula (II):

$$R^1C \equiv CR^2 \quad (II)$$

wherein $R^1$ and $R^2$ stand, independently from each other, for a monovalent group selected from:

(a) hydrogen atom, (b) an alkyl group preferably having 1–18 carbon atoms, more preferably 1–10 carbon atoms, such as methyl, ethyl, propyl, hexyl or decyl;

(e) a cycloalkyl group preferably having 5–18 carbon atoms, more preferably 5–12 carbon atoms, such as cyclohexyl, cyclooctyl or cyclododecyl;

(c) an aryl group preferably having 6–14 carbon atoms, more preferably 6–10 carbon atoms, such as phenyl, naphthyl, substituted phenyl (e.g. tolyl or benzylphenyl) or substituted naphthyl (e.g. methylnaphthyl);

(d) a heteroaryl group preferably a heterocyclic group containing oxygen, nitrogen or sulfur and having 4–12 carbon atoms, more preferably 4–8 carbon atoms, such as thienyl, furyl, pyridyl or pyrrolyl;

(e) aralkyl group preferably having 7–13 carbon atoms, more preferably 7–9 carbon atoms, such as benzyl, phenethyl, phenylbenzyl or naphthylmethyl;

(f) an alkenyl group preferably having 2–18 carbon atoms, more preferably 2–10 carbon atoms, such as vinyl, allyl or 3-butenyl;

(g) an alkoxy group preferably having 1–8 carbon atoms, more preferably 1–4 carbon atoms, such as methoxy, ethoxy or butoxy;

(h) an aryloxy group preferably having 6–14 carbon atoms, more preferably 6–10 carbon atoms, such as phenoxy or naphthyloxy;

(i) a silyl group preferably substituted with one to three alkyl groups, aryl groups, aralkyl groups and/or alkoxy groups (the alkyl, aryl, aralkyl and alkoxy groups may be as shown above), such as trimethylsilyl, triethylsilyl, triphenylsilyl, tribenzylsilyl, phenyldimethyl or trimethoxysilyl.

The groups $R^1$ and $R^2$ may contain one or more inert substituents such as methoxy, methoxycarbonyl, cyano, dimethylamino and fluoro.

Illustrative of suitable acetylene compounds are non-substituted acetylene, butyne, phenylacetylene, trimethylsilylacetylene, ethynylthiophene, diethynylbenzene, hexynenitrile and cyclohexenylacetylene. It is without saying that the present invention is not limited to these acetylene compounds.

In a first aspect of the present invention, the acetylene compound of the formula (II) is reacted with the secondary phosphite of the formula (III) in the presence of a palladium complex catalyst and water.

Any known palladium complex catalyst may be used. Low valency palladium complexes, inclusive of zero-valent complexes, may be suitably used. Low valency palladium complexes having a tertiary phosphine or a tertiary phosphite as a ligand are especially suitably used.

In this case, a precursor substance which can form in situ a low valency palladium complex having a tertiary phosphine or a tertiary phosphite as a ligand during the reaction of the acetylene compound with the secondary phosphite may also be suitably used. For example, a palladium complex containing neither tertiary phosphine nor tertiary phosphite may be used in conjunction with a tertiary phosphine or a tertiary phosphite so that a low valency palladium complex having a tertiary phosphine or a tertiary phosphite as a ligand is formed in the reaction mixture. Further, a palladium complex containing a tertiary phosphine or tertiary phosphite may be used in conjunction with another tertiary phosphine or another tertiary phosphite.

Examples of the ligands of the palladium complex catalysts include triphenylphosphine, diphenylmethylphosphine, phenyldimethylphosphine, 1,3-bis(diphenylphosphino) propane, 1,4-bis(diphenylphosphino)butane, 1,1'-bis (diphenylphosphino)ferrocene, trimethylphosphite and triphenylphosphite.

Illustrative of suitable palladium complex catalysts containing neither tertiary phosphine nor tertiary phosphite and used in conjunction with the above ligands are bis (dibenzylideneacetone)palladium and palladium acetate.

Illustrative of suitable palladium complex catalysts containing a tertiary phosphine or a tertiary phosphite are dimethylbis(triphenylphosphine)palladium, dimethylbis (diphenylmethylphosphine)palladium, ethylenebis (triphenylphosphine)palladium and tetrakis (triphenylphosphine)palladium.

Examples of palladium complex catalyst used in the present invention include (a) dimethylbis (triphenylphosphine)palladium by itself, (b) dimethylbis (diphenylmethylphosphine)palladium by itself, (c) ethylenebis(triphenylphosphine)palladium by itself, (d) tetrakis(triphenylphosphine)palladium by itself, (e) dimethylbis[1,3-bis(diphenylphosphino)propane]palladium by itself, (f) a mixture of palladium acetate with 1,3-bis (diphenylphosphino)propane, (g) a mixture of dimethylbis (diphenylmethylphosphine)palladium with 1,3-bis (diphenylphosphino)propane.

The palladium complex catalyst is used in a catalytically effective amount and, generally, in an amount of up to 20 mole %, preferably up to 5 mole %, based on the acetylene compound. The acetylene compound and the secondary phosphite are generally used in a stoichiometric amount. However, the use of the acetylene compound or the secondary phosphite in a stoichiometrically excess amount does not adversely affect the desired reaction.

The reaction is performed in the presence of water. The amount of water varies with the kind of the catalyst and is not specifically limited. Generally, however, water is used in an amount of 1–20 moles, preferably 1–10 moles, per mole of the palladium complex catalyst. The amount of water in the reaction mixture is generally 10–10,000 ppm by volume, preferably 100–5,000 ppm by volume. By addition of water, the reaction time may be reduced and the yield is improved.

The reaction may be carried out with or without using a solvent. The solvent, when used, may be a hydrocarbon solvent or an ether solvent. The reaction is generally performed from room temperature to about 200° C., preferably 50–150° C. It is preferred that the reaction be carried out in an oxygen-free atmosphere, such as in the atmosphere of nitrogen, argon, methane or ethylene.

After the termination of the reaction, the product can be separated by any known manner such as chromatography, distillation and recrystallization.

In another aspect of the present invention, the acetylene compound of the formula (II) is reacted with the secondary phosphite of the formula (III) in the presence of a palladium catalyst containing a 1,3-bisphosphinopropane of the formula (IV) as a ligand:

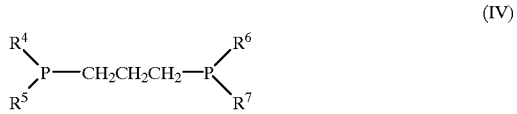

(IV)

wherein $R^4$, $R^5$, $R^6$ and $R^7$ stand, independently from each other, for:

(a) an alkyl group preferably having 1–18 carbon atoms, more preferably 1–12 carbon atoms, such as methyl, ethyl or hexyl;

(b) a cycloalkyl group preferably having 4–6 carbon atoms, more preferably 5–6 carbon atoms, such as cyclopentyl or cyclohexyl;

(c) an aralkyl group preferably having 7–13 carbon atoms, more preferably 7–9 carbon atoms, such as benzyl, phenethyl, phenylbenzyl or naphthylmethyl; or (d) an aryl group preferably having 6–14 carbon atoms, more preferably 6–10 carbon atoms, such as phenyl, naphthyl, substituted phenyl (e.g. tolyl or benzylphenyl) or substituted naphthyl (e.g. methylnaphthyl).

Low valency palladium complexes, inclusive of zero-valent complexes, having a 1,3-bisphosphinopropane of the formula (IV) as a ligand are especially suitably used.

In this case, a precursor substance which can form in situ a low valency palladium complex having a 1,3-bisphosphinopropane of the formula (IV) as a ligand during the reaction of the acetylene compound with the secondary phosphite may also be suitably used. For example, a palladium complex containing no 1,3-bisphosphinopropane of the formula (IV) may be used in conjunction with a 1,3-bisphosphinopropane of the formula (IV) so that a low valency palladium complex containing a 1,3-bisphosphinopropane of the formula (IV) is formed in the reaction mixture.

Examples of the 1,3-bisphosphinopropane of the formula (IV) include 1,3-bis(diphenylphosphino)propane, 1,3-bis(ditolylphosphino)propane, 1,3-bis(dinaphthylphosphino)propane.

Illustrative of suitable palladium complex catalysts containing no 1,3-bisphosphinopropane of the formula (IV) and used in conjunction with the above ligands are bis(dibenzylideneacetone)palladium, palladium acetate dimethylbis(triphenylphosphine)palladium and ethylenebis(triphenylphosphine)palladium.

Examples of palladium complex catalyst used in the present invention include (a) ethylene[1,3-bis-(diphenylphosphino)propane]palladium by itself, (b) styrene [1,3-bis-(diphenylphosphino)propane]palladium by itself, (c) dimethyl[1,3-bis(diphenylphosphino)propane]palladium by itself, (d) a mixture of palladium acetate with 1,3-bis(diphenylphosphino)propane, and (e) a mixture of dimethylbis(triphenylphosphine)palladium with 1,3-bis(diphenylphosphino)propane.

The palladium complex catalyst containing a 1,3-bisphosphinopropane of the formula (IV) as a ligand is used in a catalytically effective amount and, generally, in an amount of up to 20 mole %, preferably up to 5 mole %, more preferably 1–0.005 mole %, based on the acetylene compound. The acetylene compound and the secondary phosphite are generally used in a stoichiometric amount. However, the use of the acetylene compound or the secondary phosphite in a stoichiometrically excess amount does not adversely affect the desired reaction.

By using the above specific palladium complex catalyst, the reaction time may be reduced even with a small amount of the catalyst. Additionally, the use of the specific palladium catalyst permits the production of a specific isomer of unsaturated phosphonic acid esters with a high selectivity.

The reaction may be performed in the presence of water, if desired.

The reaction may be carried out with or without using a solvent. The solvent, when used, may be a hydrocarbon solvent or an ether solvent. The reaction is generally performed from room temperature to about 200° C., preferably 50–150° C. It is preferred that the reaction be carried out in an oxygen-free atmosphere, such as in the atmosphere of nitrogen, argon, methane or ethylene.

After the termination of the reaction, the product can be separated by any known manner such as chromatography, distillation and recrystallization.

The following examples will further illustrate the present invention.

COMPARATIVE EXAMPLE 1

To 1 ml of benzene were added 1 mmol of 1-octyne, 1 mmol of dimethylphosphite and 3 mol % of cis-PdMe$_2$(PPh$_3$)$_2$ (dimethylbis(triphenylphosphine)palladium) and the mixture was reacted at 67° C. for 5 hours in the atmosphere of nitrogen. The reaction mixture was distilled to obtain an isomeric mixture of (a) diethyl 1-octen-2-yl-phosphonate and (b) diethyl 1-octen-1-yl-phosphonate with a yield of 51%. The gas chromatographic analysis revealed that the weight ratio of the former phosphonate (a) to the latter phosphonate (b) was 90:10.

EXAMPLES 1–5

Comparative Example 1 was repeated in the same manner as described except that water was added in the reaction mixture in an amount as shown in Table 1 and the reaction time was changed as shown in Table 1. The yield of the isomeric mixture and the weight ratio of diethyl 1-octen-2-yl-phosphonate to diethyl 1-octen-1-yl-phosphonate are summarized in Table 1.

TABLE 1

| Example | Amount of Water | | Reaction Time (hour) | Total Yield (%) (a/b ratio) |
|---|---|---|---|---|
| | Water/ Catalyst Molar Ratio | Concentration in Reaction Mixture (ppm v/v) | | |
| 1 | 1 | 242 | 6 | 88 (94/6) |
| 2 | 2 | 806 | 6 | 100 (94/6) |
| 3 | 4 | 1,613 | 1.5 | 100 (94/6) |
| 4 | 8 | 3,227 | 1.5 | 100 (94/6) |
| 5 | 12 | 4,840 | 10 | 53 (94/6) |

EXAMPLES 6 AND 7

Example 3 was repeated in the same manner as described except that 1-octyne was substituted by acetylene (Example 6) or phenylacetylene (Example 7), thereby obtaining dimethyl vinylphosphonate with a yield of 87% (Example 6) and α- and β-dimethyl phenylvinylphosphonates with a yield of 92% (Example 7, α/β molar ratio: 98/2).

COMPARATIVE EXAMPLE 2

A mixture of 1 mmol of 1-octyne, 1 mmol of dimethylphosphite and 0.005 mmol of cis-PdMe$_2$(PPh$_2$Me)$_2$ (dimethylbis(diphenylmethylphosphine)palladium) and the mixture was reacted at 100° C. for 18 hours in the atmosphere of nitrogen. The reaction mixture was distilled to obtain an isomeric mixture of (a) dimethyl 1-octen-2-yl-phosphonate and (b) dimethyl 1-octen-1-yl-phosphonate with a yield of 78%. The gas chromatographic analysis revealed that the weight ratio of the former phosphonate (a) to the latter phosphonate (b) was 91:9.

EXAMPLE 8

A mixture of 5 mmol of 1-octyne, 5 mmol of dimethylphosphite and 0.025 mmol of palladium acetate and 1,3-bis(diphenylphosphino)propane (1.5 equivalents based on the palladium acetate) was reacted at 100° C. for 6 hours in the atmosphere of nitrogen. The proton NMR analysis of the resulting reaction mixture revealed that an isomeric mixture of (a) dimethyl 1-octen-2-yl-phosphonate and (b) dimethyl 1-octen-1-yl-phosphonate was obtained with a yield of 100% and that the weight ratio of the former phosphonate (a) to the latter phosphonate (b) was 98:2.

EXAMPLE 9

Example 8 was repeated in the same manner as described except that the amount of each of palladium acetate and 1,3-bis(diphenylphosphino)propane was reduced to 1/10 and that the reaction was performed at 100° C. for 36 hours. The proton NMR analysis of the resulting reaction mixture revealed that an isomeric mixture of (a) dimethyl 1-octen-2-yl-phosphonate and (b) dimethyl 1-octen-1-yl-phosphonate was obtained with a yield of 100% and that the weight ratio of the former phosphonate (a) to the latter phosphonate (b) was 98:2.

EXAMPLES 10 AND 11

Example 8 was repeated in the same manner as described except that 1-octyne was substituted by acetylene (Example 10) or phenylacetylene (Example 11), thereby obtaining dimethyl vinylphosphonate with a yield of 82% (Example 10) and α- and β-dimethyl phenylvinylphosphonates with a yield of 85% (Example 11, α/β molar ratio: 99/1).

EXAMPLE 12

Example 8 was repeated in the same manner as described except that 1,3-bis(dimethylphosphino)propane was substituted for 1,3-bis(diphenylphosphino)propane and that the reaction was carried out for 36 hours. The proton NMR analysis of the resulting reaction mixture revealed that an isomeric mixture of (a) dimethyl 1-octen-2-yl-phosphonate and (b) dimethyl 1-octen-1-yl-phosphonate was obtained with a yield of 85% and that the weight ratio of the former phosphonate (a) to the latter phosphonate (b) was 94:6.

What is claimed is:

1. A process for the preparation of an unsaturated phosphonic acid ester of the following formula (I):

wherein $R^1$ and $R^2$ stand, independently from each other, for a monovalent group selected from hydrogen atom, an alkyl group, a cycloalkyl group, an aryl group, a heteroaryl group, aralkyl group, an alkenyl group, an alkoxy group, an aryloxy group and a silyl group and $R^3$ stands for an alkyl group, a cycloalkyl group, an aralkyl group or an aryl group, comprising reacting an acetylene compound of the following formula (II):

wherein $R^1$ and $R^2$ are as defined above, with a secondary phosphite of the following formula (III):

wherein $R^3$ is as defined above, in the presence of a palladium complex catalyst, characterized in that said reaction of the acetylene compound with the secondary phosphite is performed in the presence of water.

2. A process as claimed in claim 1, wherein said water is present in an amount of 1–20 moles per mole of said palladium complex catalyst.

3. A process for the preparation of an unsaturated phosphonic acid ester of the following formula (I):

wherein $R^1$ and $R^2$ stand, independently from each other, for a monovalent group selected from hydrogen atom, an alkyl group, a cycloalkyl group, an aryl group, a heteroaryl group, aralkyl group, an alkenyl group, an alkoxy group, an aryloxy group and a silyl group and $R^3$ stands for an alkyl group, a cycloalkyl group, an aralkyl group or an aryl group, comprising reacting an acetylene compound of the following formula (II):

wherein $R^1$ and $R^2$ are as defined above, with a secondary phosphite of the following formula (III):

wherein $R^3$ is as defined above, characterized in that said palladium complex catalyst contains, as a ligand, a 1,3-bisphosphinopropane of the following formula (IV):

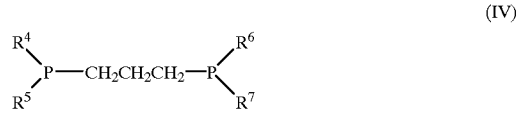

wherein $R^4$, $R^5$, $R^6$ and $R^7$ stand, independently from each other, for an alkyl group, a cycloalkyl group, an aralkyl group or an aryl group.

4. A process as claimed in claim 3, wherein said palladium complex catalyst additionally contains a carboxylic acid residue as a ligand.

5. A process as claimed in claim 3, wherein said reaction is performed in the presence of water.

* * * * *

UNITED STATES PATENT AND TRADEMARK OFFICE
CERTIFICATE OF CORRECTION

PATENT NO. : 6,111,127
DATED : August 29, 2000
INVENTOR(S) : Tanaka et al.

It is certified that error appears in the above-identified patent and that said Letters Patent is hereby corrected as shown below:

<u>Title page,</u>
"Item [73] Assignees: Agency of Industrial Science and Technology; Masato Tanaka, both of Japan" should read -- [73] Assignees: Director-General of Agency of Industrial Science and Technology; Masato Tanaka, both of Japan --.

Signed and Sealed this

Twentieth Day of November, 2001

Attest:

*Nicholas P. Godici*

NICHOLAS P. GODICI
*Acting Director of the United States Patent and Trademark Office*

*Attesting Officer*